United States Patent [19]

Carson

[11] 4,294,760
[45] Oct. 13, 1981

[54] PREPARATION OF 5-(ARYLCYANOHYDROXYMETHYL)-1-LOWERALKYLPYRROLE-2-ACETIC ACID DERIVATIVES

[75] Inventor: John R. Carson, Norristown, Pa.

[73] Assignee: McNeilab, Inc., Fort Washington, Pa.

[21] Appl. No.: 141,438

[22] Filed: Apr. 17, 1980

[51] Int. Cl.³ .......................................... C07D 207/337
[52] U.S. Cl. ......................... 260/326.47; 260/326.5 R; 260/326.5 S; 260/545 R
[58] Field of Search ..................... 260/326.47, 326.5 S, 260/326.5 R

[56] References Cited

U.S. PATENT DOCUMENTS 4,255,335  3/1981  Carson .......................... 260/326.47

OTHER PUBLICATIONS

Jones et al., The Chemistry of Pyrroles, (Academic Press, N.Y., 1977), pp. 164–166, 169–172, 304.
Selikson et al., J. Org. Chem., vol. 40, pp. 267–268 (1975).

Primary Examiner—Alton D. Rollins

[57] ABSTRACT

5-(Arylcyanohydroxymethyl)-1-loweralkylpyrrole-2-acetic acid derivatives are prepared by the protic acid catalyzed reaction of aroylcyanides with 1-loweralkylpyrrole-2-acetic acid derivatives, which is then converted by treatment with alkali metal hydroxides or heat to form 5-aroyl-1-loweralkylpyrrole-2-acetic acid or derivatives thereof.

6 Claims, No Drawings

PREPARATION OF 5-(ARYLCYANOHYDROXYMETHYL)-1-LOWERALKYLPYRROLE-2-ACETIC ACID DERIVATIVES

This invention relates to novel 5-(arylcyanohydroxymethyl)-1-loweralkylpyrrole-2-acetic acid derivatives (III), a process for their preparation, and a process for their conversion to known 5-aroyl-1-loweralkyl pyrrole-2-acetic acids and derivatives thereof. They are prepared by the reaction of aroylcyanides (I) with 1-loweralkylpyrrole-2-acetic acid derivatives (II). The reaction is carried out in an inert, aprotic solvent in the presence of a protic acid catalyst. Products of type III may be utilized by their conversion by mild treatment with alkali metal hydroxides or by heating to 5-aroyl-1-loweralkylpyrrole-2-acetic acid derivatives (IV). Materials of formula IV are known to be useful in the manufacture of 5-aroyl-1-loweralkylpyrrole-2-acetic acids (V) and their alkali metal salts which are useful as anti-inflammatory agents (Carson, U.S. Pat. No. 3,752,826). Alternatively, products of type III may be directly converted to products of type V by more strenuous treatment with alkali metal hydroxide solutions. Also, it is not necessary to isolate III to prepare IV or V, and such processes are also included in the present invention.

The reactions are as set forth in the following schematic diagram:

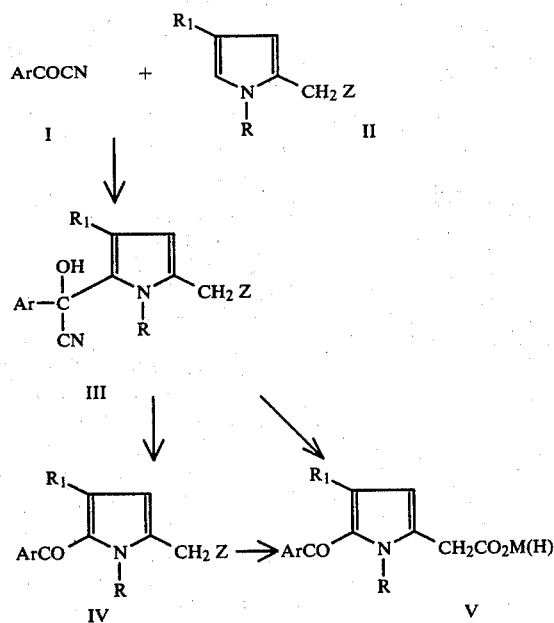

wherein:
Ar represents phenyl or phenyl substituted by a member selected from the group consisting of loweralkyl, halo, nitro, methylthio, trifluoromethyl, and loweralkoxy;
R represents loweralkyl;
$R_1$ represents hydrogen or loweralkyl;
Z represents —CN or —COO(loweralkyl);
HX represents any moderately strong to strong acid having a pK< about 2, for example, $Cl_3CCO_2H$, $CF_3CO_2H$, $HO_2CCO_2H$, HCl, $HClO_4$, $CH_3SO_3H$, P-tolyl $SO_3H$; and M represents alkali metal, for example Na, K.

As used herein, "loweralkyl" and "loweralkoxy" may be straight or branch chained saturated hydrocarbons having from one to six carbon atoms, such as, for example, methyl, ethyl, propyl, isopropyl, butyl, pentyl, hexyl and the like alkyls, and respectively, the corresponding alkoxys, such as methoxy, ethoxy, propoxy, isopropoxy, etc.

ADVANTAGES

Several disadvantages are inherent in known processes for the production of products of type IV. The Friedel-Crafts aroylation of 1-loweralkylpyrrole-2-acetic acid derivatives (II) produces a mixture of 4- and 5-aroyl-1-loweralkylpyrrole-2-acetic acid derivatives. [J. R. Carson and S. Wong, J. Med. Chem., 14, 647 (1971)]. Uncatalyzed aroylation of 1-loweralkylpyrrole-2-acetic acid derivatives (Carson, U.S. Pat. No. 3,998,844) is carried out at high temperatures and produces hydrogen chloride which can induce polymerization of pyrroles [Advances in Heterocyclic Chemistry, ed. Katritsky, Vol. 2, p. 287, Academic Press, New York (1963)]. The present invention produces no isomeric by-products. It is operated at moderate temperatures and only catalytic quantities of acid are used.

UTILITY

The final products (V) made by the processes of the present invention are known compounds disclosed in U.S. Pat. No. 3,752,826 and other literature which are useful as anti-inflammatory agents and analgesics, and include tolmetin sodium, i.e, sodium 1-methyl-5-p-toluoylpyrrole-2-acetate dihydrate and zomepirac sodium, i.e., sodium 5-(4-chlorobenzoyl)-1,4-dimethyl-1H-pyrrole-2-acetate dihydrate among the better known members of this class of compounds.

DETAILED DESCRIPTION

The protic acid catalyzed reaction of an aroylcyanide (I) with a 1-loweralkylpyrrole-2-acetic acid derivative (II) to give a 5-(arylcyanohydroxymethyl)-1-loweralkylpyrrole-2derivative (III) is carried out as follows:

Approximately equivalent quantities of reactants I and II are employed. The reaction is carried in an inert aprotic solvent such as diethylether, tetrahydrofuran, benzene, toluene, acetonitrile, ethyl acetate, methylene chloride, chloroform, or acetone. The reaction is carried out at a relatively low temperature of about 0°–40° C., preferably 25° C. An acid with a pK below about 2 is employed, for example: trichloroacetic acid, perchloric acid, methanesulfonic acid, oxalic acid, p-toluenesulfonic acid. The acid catalyst is used in about 1–5 molar percent quantities. The 5-(arylcyanohydroxymethyl)-1-loweralkylpyrrole-2-acetic acid derivative III may be isolated directly from the reaction mixture, for example by filtration. Alternatively, they may be employed without purification as intermediate to IV and V.

The conversion of a substance of type III to the corresponding derivative, IV, can be carried by heating at a temperature in excess of about 100°. This conversion may be carried in the presence of an inert solvent, for example, xylene. Alternatively, the conversion is carried out by mild treatment with a base, for example, by dissolving III in an inert, aprotic solvent and shaking it with a base such as NaOH or KOH.

The conversion of III to V is carried out by hydrolysis with an alkali metal hydroxide, preferably sodium hydroxide. A precipitate of the V in the form of its alkali metal salt is collected by filtration.

PREPARATION OF STARTING MATERIALS

The aroylcyanides used as starting materials for the present invention are known compounds or classes of compounds. Thus, those aroylcyanides (I) wherein Ar is phenyl or phenyl substituted by loweralkyl, halo, and loweralkoxy are disclosed in Koenig & Weber, *Tet. Let.*, 2275 (1974). While that article only teaches individual compounds other members of the class may be made in the same manner there described. Those aroylcyanide (I) compounds wherein Ar is nitrophenyl are disclosed in Normant & Piechucki, *Bull. Soc. Chem. France*, 2402 (1972). The aroylcyanide compounds wherein Ar represent trifluoromethylphenyl and methylthiophenyl are not known, but can be made by the procedure taught by Normant & Piechucki above, i.e., by reacting p-methylthiobenzoyl chloride or m-trifluoromethylbenzoyl chloride, with copper cyanide in the presence of methylcyanide, the desired aroylcyanide products will be obtained.

The loweralkylpyrrole-2-acetic acid derivatives (II) wherein Z represents $CO_2$loweralkyl are known compounds, as disclosed in U.S. Pat. No. 3,752,826 in Examples CXI and CXXI. Those compounds in (II), wherein Z represents CN, are disclosed in U.S. Pat. No. 3,957,818.

The following examples are intended to illustrate, but not to limit the scope of the present invention. All temperatures therein are in degrees Celsius (°C.).

EXAMPLE I

Methyl-5-(cyanohydroxyphenylmethyl)-1-methylpyrrole-2-acetate

A solution of 6.7 g (0.05 mole) of benzoylcyanide, 7.6 g (0.05 mole) of methyl 1-methylpyrrole-2-acetate and 0.2 g of trichloroacetic acid in 20 ml. of ether was stirred for four days at 25° C. under argon. The solution was cooled to 0° and the solid methyl 5-(cyanohydroxyphenylmethyl)-1-methylpyrrole-2-acetate was collected by filtration; mp 148°–153°, yield, 4.0 g (28 percent).

EXAMPLE II(A)

Methyl 5-[cyanohydroxy(4-methylphenyl)methyl]-1-methylpyrrole-2-acetate

A solution of 1.45 g (0.01 mole) of 4-methylbenzoylcyanide, 1.5 g (0.01 mole) of methyl 1-methylpyrrole-2-acetate and 40 mg (0.25 mmoles) of trichloroacetic acid in 4 ml of ether was stirred at 25° under nitrogen for 21 days. The precipitated solid was collected by filtration and washed with cold ether, than hexane. The combined filtrates were evaporated in vacuo. A second crop of crystals was taken from hexane. After recrystallization from toluene:hexane was obtained, 0.46 g (16 percent yield) of methyl 5-[cyanohydroxy(4-methylphenyl)-methyl]-1-methylpyrrole-2-acetate mp 117°–118°. $H^1$ NMR $CDCl_3$ 2.35 (s, 3 H); 3.35 (s, 3 H); 3.55 (s, 2H); 3.65 (s, 3 H); 5.90 (d, 1 H); 6.05 (d, 1H); 7.15 (d, 2H); 7.35 (d, 2H). MS m/e 281, 280, 266, 212 $IR^{nujol}$ 3425, 1700 $cm^{-1}$.

EXAMPLE II(B)

Following the procedure of Example II(A), but replacing the 4-methylbenzoylcyanide with each of the following:

3-propylbenzoylcyanide;
4-methoxybenzoylcyanide;
4-chlorobenzoylcyanide;
4-nitrobenzoylcyanide;
4-methylthiobenzoylcyanide;
3-trifluoromethylbenzoylcyanide, thee can be obtained the following, respectively:

methyl 5-[cyanohydroxy(3-propylphenyl)methyl]-1-methylpyrrole-2-acetate;
methyl 5-[cyanohydroxy(4-methoxyphenyl)methyl]-1-methylpyrrole-2-acetate;
methyl 5-[(4-chlorophenyl)cyanohydroxymethyl]-1-methylpyrrole-2-acetate;
methyl 5-[cyanohydroxy(4-nitrophenyl)methyl]-1-methylpyrrole-2-acetate;
methyl 5-[cyanohydroxy(4-methylthiophenyl)methyl]-1-methylpyrrole-2-acetate.
methyl 5-[cyanohydroxy(3-trifluoromethylphenyl)-methyl]-1-methylpyrrole-2-acetate.

EXAMPLE III

Methyl 1-methyl-5-(cyanohydroxyphenylmethyl)pyrrole-2-acetate

Benzoyl cyanide, 0.67 g (0.005 mole) and methyl 1-methylpyrrole-2-acetate, 0.76 g (0.005 mole) were stirred together in ether (2 ml) containing oxalic acid (0.04 g). The reaction was run in the dark at room temperature. After six days, the reaction mixture was placed in the freezer overnight, filtered, and washed with cold ether to yield 0.17 g (12 percent) of methyl 1-methyl-5-(cyanohydroxyphenylmethyl)pyrrole-2-acetate, mp 137°–8°. The solid state IR spectrum was identical to authentic material.

EXAMPLE IV(A)

1-Methyl-5-(4-methylbenzoyl)pyrrole-2-acetonitrile

A solution of 0.16 g (1.1 mmole) of 4-methylbenzoylcyanide, 0.13 g (1.1 mmole) of 1-methylpyrrole-2-acetonitrile and 4 mg of trichloroacetic acid in 0.4 ml of ether was allowed to stand in the dark under nitrogen at 25°. After three days, a small amount of hydrogen chloride gas was admitted to the vessel. The mixture was allowed to stand for 14 days. It was diluted with methylene chloride and the solution washed with sodium hydroxide. The solution was dried ($MgSO_4$) and the solvent evaporated in vacuo. The residue was chromatographed on 37 ml of silica gel. The fractions eluted with a mixture of 1,1,1-trichloroethane:hexane, 1:1 were discarded. The fractions eluted with 1,1,1-trichloroethane:hexane 3:1 were collected. The solvent was evaporated to give 0.80 g of dark solid 1-methyl-5-(4-methylbenzoyl)pyrrole-2-acetonitrile (30 percent yield). It was recrystallized from 1,1,1-trichloroethane:hexane to give brown solid, mp 103°–104°, undepressed by admixture with authentic material.

EXAMPLE IV(B)

Following the procedure of Example IV(A), but replacing the 4-methylbenzoylcyanide with each of the following:

3-propylbenzoylcyanide;
4-methoxybenzoylcyanide;
4-chlorobenzoylcyanide;
4-nitrobenzoylcyanide;
4-methylthiobenzoylcyanide;
3-trifluoromethylbenzoylcyanide, there can be obtained the following, respectively:
1-methyl-5-(3-propylbenzoyl(pyrrole-2-acetonitrile;
1-methyl-5-(4-methoxybenzoyl)pyrrole-2-acetonitrile;
1-methyl-5-(4-chlorobenzoyl)pyrrole-2-acetonitrile;
1-methyl-5-(4-nitrobenzoyl)pyrrole-2-acetonitrile;
1-methyl-5-(4-methylthiobenzoyl)pyrrole-2-acetonitrile;
1-methyl-5-(3-trifluoromethylbenzoyl)pyrrole-2-acetonitrile.

EXAMPLE V

Methyl 1-methyl-5-(4-methylbenzoyl)pyrrole-2-acetate

Methyl 5-[cyanohydroxy(4-methylphenyl)methyl]-1-methylpyrrole-2-acetate (0.161 g, 0.540 mmoles) was dissolved in 30 ml of ether and shaken with 10 percent NaOH, washed with brine and dried over $MgSO_4$. Evaporation of the ether yielded 0.130 g (86.1 percent) of methyl 1-5-(4-methylbenzoyl)pyrrole-2-acetate, mp 118°–120°. The IR was identical to an authentic sample of methyl 1-methyl-5-(4-methylbenzoyl)pyrrole-2-acetate.

EXAMPLE VI

5-Benzoyl-1-methylpyrrole-2-acetic acid

A suspension of 1.0 g of methyl 5-(cyanohydroxyphenylmethyl)-1-methylpyrrole-2-acetate in 20 ml of 5 percent sodium hydroxide solution was heated under reflux for 30 minutes. The solution was acidified with 3 N hydrochloric acid solution. The solid was collected and recrystallized from acetonitrile to give 0.61 g (77 percent yield) of white crystalline 5-benzoyl-1-methylpyrrole-2-acetic acid, mp 145°–6°, undepressed by admixture with authentic product.

EXAMPLE VII

1-Methyl-5-(4-methylbenzoyl)pyrrole-2-acetic acid

Methyl 5-[cyanohydroxy(4-methylphenyl)methyl]-1-methylpyrrole-2-acetate, 55 mg (0.185 mmole) was heated on a steam bath in 15 percent NaOH (1.5 ml) for 3.5 hours. The reaction was cooled on ice for one hour then filtered. The solid was dissolved in distilled water, hot filtered, cooled, 3 N HCl was added to precipitate 0.48 g (100 percent) of 1-methyl-5-(4-methylbenzoyl)-pyrrole-2-acetic acid, mp 153°–158°, undepressed by admixture with authentic material.

EXAMPLE VIII(A)

Sodium 1-methyl-5-(4-methylbenzoyl)pyrrole-2-acetate dihydrate

A mixture of 1.45 g (0.01 mole) of 4-methylbenzoylcyanide, 1.53 g (0.01 mole) of methyl 1-methylpyrrole-2-acetate, 0.04 g (0.25 mmole) of trichloroacetic acid, and 0.5 ml of ether was stirred under nitrogen for 22.5 hours at 25°.

A 17 ml portion of 10 percent sodium hydroxide solution was added and the mixture heated under reflux for three hours. The solution was cooled and the precipitated solid was collected by filtration and washed with cold 95 percent ethanol. The solid was recrystallized from 95 percent ethanol to give 1.03 g (37 percent yield) of sodium 1-methyl-5-(4-methylbenzoyl)pyrrole-2-acetate, mp 299°–300°. The solid state IR was identical to authentic material.

EXAMPLE VIII(B)

Following the procedure of Example VIII(A), but replacing the 4-methylbenzoylcyanide with each of the following aroylcyanides:
3-propylbenzoylcyanide;
4-methoxybenzoylcyanide;
4-bromobenzoylcyanide;
4-nitrobenzoylcyanide;
4-methylthiobenzoylcyanide;
3-trifluoromethylbenzoylcyanide,
there can be obtained the following, respectively:
sodium 1-methyl-5-(3-propylbenzoyl)pyrrole-2-acetate dihydrate;
sodium 1-methyl-5-(4-methoxybenzoyl)pyrrole-2-acetate dihydrate;
sodium 1-methyl-5-(4-bromobenzoyl)pyrrole-2-acetate dihydrate;
sodium 1-methyl-5-(4-nitrobenzoyl)pyrrole-2-acetate dihydrate;
sodium 1-methyl-5-(4-methylthiobenzoyl)pyrrole-2-acetate dihydrate;
sodium 1-methyl-5-(3-trifluoromethylbenzoyl)pyrrole-2-acetate dihydrate.

EXAMPLE IX

Methyl 5-benzoyl-1-methylpyrrole-2-acetate

A 0.25 g sample of methyl 5-(cyanohydroxyphenylmethyl)-1-methylpyrrole-2-acetate in 2 ml of xylene was heated at 140° C. for 2 hours. The solution was cooled and methylcyclohexane added. There was obtained 0.16 g (70 percent yield) of a gray solid. It was recrystallized to give white solid methyl 5-benzoyl-1-methylpyrrole-2-acetate, mp 96°–98° C., undepressed by admixture with authentic material.

EXAMPLE X

Ethyl 5-(4-chlorobenzoyl)-1,4-dimethylpyrrole-2-acetate

A solution of 1.65 g (0.01 mole) of p-chlorobenzoylcyanide, 1.81 g (0.01 mole) of ethyl 1,4-dimethylpyrrole-2-acetate and 0.08 g of anhydrous oxalic acid in 4 ml of ether was stored in the dark under nitrogen for four days. The solution was diluted with $CH_2Cl_2$. The organic solution was washed with 10 percent NaOH solution, dried ($MgSO_4$), and the solvent evaporated in vacuo. The residue was recrystallized from 1,1,1-trichloroethane to give 1.04 g of ethyl 5-(4-chlorobenzoyl)-1,4-dimethylpyrrole-2-acetate, mp 105°–108° C., undepressed by admixture with authentic material.

I claim:
1. A 5-(arylcyanohydroxymethyl)-1-loweralkylpyrrole-2-acetic acid derivative having the formula:

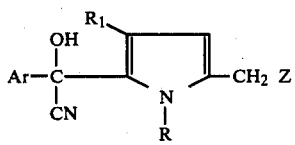

wherein:
R is loweralkyl;
$R_1$ is hydrogen or loweralkyl;
Z is CN or COO(loweralkyl); and
Ar is phenyl or phenyl substituted with a substituent selected from the group consisting of loweralkyl, halo, nitro, methylthio, trifluoromethyl, and loweralkoxy.

2. A compound of claim 1, which is methyl 5-(cyanohydroxyphenylmethyl)-1-methylpyrrole-2-acetate.

3. A compound of claim 1, which is methyl 5-[cyanohydroxy(4-methylphenyl)methyl]-1-methylpyrrole-2-acetate.

4. A compound of claim 1, which is ethyl 5-[(4-chlorophenyl)cyanohydroxymethyl]-1,4-dimethylpyrrole-2-acetate.

5. A compound of claim 1, which is 1-methyl-5-[cyanohydroxy(4-methylphenyl)methyl]pyrrole-2-acetonitrile.

6. The process of preparing 5-(arylcyanohydroxymethyl)-1-loweralkylpyrrole-2-acetic acid derivatives of formula:

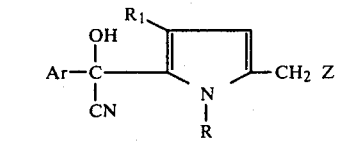

which comprises reacting an aroylcyanide of formula:

ArCOCN with a 1-loweralkylpyrrole-2-acetic acid derivative of formula:

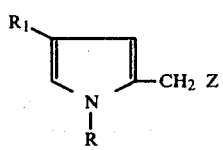

in the presence of an acid of pK below about 2, in an inert aprotic solvent at a temperature between 0° and 40° C., wherein in the foregoing formulae:
R is loweralkyl;
$R_1$ is hydrogen or loweralkyl;
Z is CN OR COO(loweralkyl);
Ar is phenyl or phenyl substituted with a substituent selected from the group consisting of loweralkyl, halo, nitro, methylthio, trifluoromethyl and loweralkoxy.

* * * * *